(12) United States Patent
Nakagawa

(10) Patent No.: US 11,971,534 B2
(45) Date of Patent: Apr. 30, 2024

(54) OPTICAL TRANSDUCER FOR ENDOSCOPE, ENDOSCOPE, AND MANUFACTURING METHOD OF OPTICAL TRANSDUCER FOR ENDOSCOPE

(71) Applicant: OLYMPUS CORPORATION, Tokyo (JP)

(72) Inventor: Yusuke Nakagawa, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 350 days.

(21) Appl. No.: 17/395,938

(22) Filed: Aug. 6, 2021

(65) Prior Publication Data

US 2021/0373317 A1 Dec. 2, 2021

Related U.S. Application Data

(63) Continuation of application No. PCT/JP2019/008543, filed on Mar. 5, 2019.

(51) Int. Cl.
*G02B 23/24* (2006.01)
*A61B 1/04* (2006.01)
*G02B 6/42* (2006.01)

(52) U.S. Cl.
CPC ........... *G02B 23/2423* (2013.01); *A61B 1/04* (2013.01); *G02B 23/2469* (2013.01); *G02B 6/4243* (2013.01)

(58) Field of Classification Search
CPC .... G02B 6/30; G02B 6/4248; G02B 23/2423; G02B 23/2469; G02B 6/4243; G02B 6/423; G02B 6/4221; G02B 6/4239; G02B 6/424; A61B 1/04; A61B 1/00; A61B 1/05
See application file for complete search history.

(56) References Cited

U.S. PATENT DOCUMENTS

| 2015/0086162 A1* | 3/2015 | Miyahara ........... G02B 23/2446 385/33 |
| 2017/0315310 A1 | 11/2017 | Nakagawa |
| 2018/0078114 A1 | 3/2018 | Kobayashi |

FOREIGN PATENT DOCUMENTS

| JP | 2007-079175 A | 3/2007 |
| JP | 2015-179207 A | 10/2015 |
| WO | 2015/141577 A1 | 9/2015 |
| WO | 2016/117121 A1 | 7/2016 |

(Continued)

OTHER PUBLICATIONS

International Search Report dated Apr. 23, 2019 received in PCT/JP2019/008543.

*Primary Examiner* — Ryan A Lepisto
*Assistant Examiner* — Erin D Chiem
(74) *Attorney, Agent, or Firm* — Scully, Scott, Murphy & Presser, P.C.

(57) ABSTRACT

An optical transducer for endoscope includes an optical element, an optical fiber, and a ferrule, the ferrule including a semiconductor substrate and a glass substrate, in which: the semiconductor substrate has an insertion hole penetrating therethrough; an optical fiber is inserted into the insertion hole; the semiconductor substrate has a trench connected with the insertion hole and having an opening in a side surface; the trench has a convex on a bottom surface; and when a distal end surface of the optical fiber is observed from an opening of side surface of the tech, at least a part of the distal end surface is shielded by the convex.

20 Claims, 7 Drawing Sheets

(56) References Cited

FOREIGN PATENT DOCUMENTS

WO     2016/157301 A1    10/2016
WO     2016/189691 A1    12/2016

\* cited by examiner

OPTICAL TRANSDUCER FOR ENDOSCOPE, ENDOSCOPE, AND MANUFACTURING METHOD OF OPTICAL TRANSDUCER FOR ENDOSCOPE

CROSS REFERENCE TO RELATED APPLICATION

This application is a continuation application of PCT/JP2019/008543 filed on Mar. 5, 2019, the entire contents of which are incorporated herein by this reference.

BACKGROUND OF THE INVENTION

1. Field of the Invention

The present invention relates to an optical transducer for endoscope including a ferrule having an insertion hole in which an optical fiber is inserted and is fixed by transparent resin, an endoscope including the optical transducer for endoscope including a ferrule having an insertion hole in which an optical fiber is inserted and is fixed by transparent resin, and a manufacturing method of the optical transducer for endoscope including a ferrule having an insertion hole in which an optical fiber is inserted and is fixed by transparent resin.

2. Description of the Related Art

An endoscope includes an image pickup device in a distal end portion of an elongated insertion portion. In recent years, an image pickup device having a large number of pixels has been studied to display high-quality images. When an image pickup device having a large number of pixels is used, the amount of image signals to be transmitted from the image pickup device to a signal processor increases.

In order to reduce the diameter and invasiveness of the insertion portion, it is preferable to use optical signal transmission via a thin optical fiber by using an optical signal instead of an electric signal. For optical signal transmission, an E/O type optical transducer (electrical-optical converter) that converts an electric signal into an optical signal and an O/E type optical transducer (optical-electrical converter) that converts an optical signal into an electric signal are used.

In order to reduce the diameter of the insertion portion of an endoscope, it is important to reduce the size of the optical transducer.

International Publication No. 2016/157301 discloses an optical transducer for endoscope in which an injection hole is provided in an insertion hole of a ferrule for injecting a resin for fixing an optical fiber to the insertion hole in which the optical fiber is inserted. The optical fiber inserted into the insertion hole is optically coupled with an optical element arranged so as to oppose the insertion hole.

SUMMARY OF THE INVENTION

An optical transducer for endoscope according to an embodiment includes: at least one optical element; at least one optical fiber optically coupled with the optical element; and a ferrule including a semiconductor substrate including a first principal surface and a second principal surface opposite to the first principal surface, and a glass substrate including a third principal surface and a fourth principal surface opposite to the third principal surface and configured such that the third principal surface is bonded with the second principal surface, wherein at least one insertion hole penetrates the semiconductor substrate, the optical fiber is inserted into the insertion hole, and the optical element is mounted on the fourth principal surface, wherein the semiconductor substrate includes at least one trench penetrating through the semiconductor substrate, connected with the at least one insertion hole, and having an opening in a side surface of the semiconductor substrate, the optical fiber is fixed to the ferrule with a transparent resin arranged in the insertion hole and the trench, the third principal surface which is a bottom surface of the trench includes a convex, and when a distal end surface of the optical fiber is observed from the opening of the trench in the side surface, at least a part of the distal end surface is shielded by the convex.

An endoscope according to an embodiment includes an optical transducer for endoscope, wherein the optical transducer for endoscope includes: at least one optical element; at least one optical fiber optically coupled with the optical element; and a ferrule including a semiconductor substrate including a first principal surface and a second principal surface opposite to the first principal surface, and a glass substrate including a third principal surface and a fourth principal surface opposite to the third principal surface and configured such that the third principal surface is bonded with the second principal surface, wherein at least one insertion hole penetrates the semiconductor substrate, the optical fiber is inserted into the insertion hole, and the optical element is mounted on the fourth principal surface, wherein the semiconductor substrate includes at least one trench penetrating through the semiconductor substrate, connected with the at least one insertion hole, and having an opening in a side surface of the semiconductor substrate, the optical fiber is fixed to the ferrule with a transparent resin arranged in the insertion hole and the trench, the third principal surface which is a bottom surface of the trench includes a convex, and when a distal end surface of the optical fiber is observed from the opening of the trench in the side surface, at least a part of the distal end surface is shielded by the convex.

In a manufacturing method of an optical transducer for endoscope according to an embodiment, the optical transducer for endoscope includes: at least one optical element; at least one optical fiber optically coupled with the optical element, and a ferrule including a semiconductor substrate including a first principal surface and a second principal surface opposite to the first principal surface, and a glass substrate including a third principal surface and a fourth principal surface opposite to the third principal surface and configured such that the third principal surface is bonded with the second principal surface, wherein at least one insertion hole penetrates the semiconductor substrate, the optical fiber is inserted into the insertion hole, and the optical element is mounted on the fourth principal surface, wherein the semiconductor substrate includes at least one trench penetrating through the semiconductor substrate, connected with the insertion hole, and having an opening in a side surface of the semiconductor substrate, the optical fiber is fixed to the ferrule with a transparent resin arranged in the insertion hole and the trench, the third principal surface which is a bottom surface of the trench includes a convex, and when a distal end surface of the optical fiber is observed from the opening of the trench in the side surface, at least a part of the distal end surface is shielded by the convex, the manufacturing method of the optical transducer for endoscope including: when the insertion hole and the trench are formed by an etching method on a stacked substrate in which the semiconductor substrate and the glass substrate are stacked, ending etching in a state in which the third principal surface is exposed on a bottom surface of the trench, and the convex remains on a part of the bottom surface; mounting the optical element on the stacked substrate; inserting the optical fiber into the insertion hole, and observing a distal end surface of the optical fiber from a side surface of the ferrule to confirm that at least a part of the distal end surface is shielded by the convex, arranging uncured transparent resin in the insertion hole via the trench; and curing the transparent resin of an ultraviolet curable type or an ultraviolet/thermal dual-curable type.

DETAILED DESCRIPTION OF THE PREFERRED EMBODIMENTS

First Embodiment

Referring to FIGS. 1 to 6, an optical transducer for endoscope 1 (hereinafter, may be referred to as "optical transducer 1") of a first embodiment will be described. Note that in the following description, drawings based on respective embodiments are schematic. Relationship between the thickness and width of each part, ratios of the thickness of respective parts, and the like are different from the actual ones. The drawings may also include some parts the dimensional relationships and ratios of which are mutually different among the drawings. Illustration of some components and designation of reference symbols are omitted.

Figure 15:
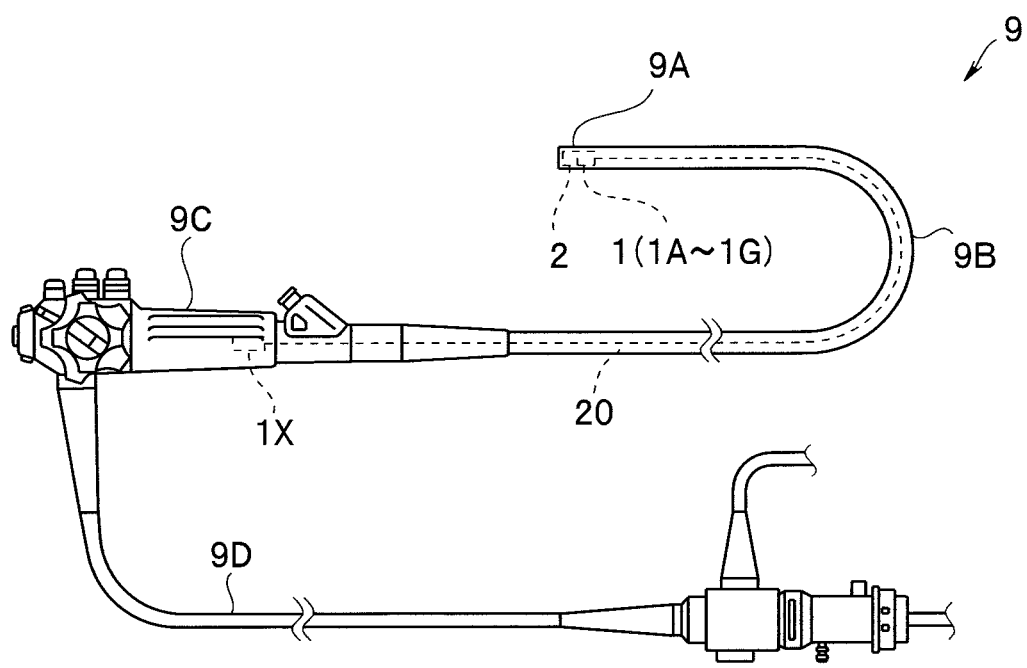
FIG. 15 is an external view of an endoscope according to a third embodiment.

The optical transducer 1 is an ultra-small size E/O type module (electrical-optical converter) which is configured to convert an electric signal outputted by an image pickup device 2 of an endoscope 9 into an optical signal and transmit the optical signal (see FIG. 15).

The optical transducer 1 includes an optical element 10, an optical fiber 20, and a ferrule 30.

The optical element 10 is a light emitting element including a light emitting region 11 that outputs an optical signal. For example, an ultra-small size optical element 10 having a plan view dimension of 235 μm×235 μm includes, on a light emitting surface 10SA, a light emitting region 11 having a diameter of 10 μm and configured to output optical signals, two external electrodes 12 each having a diameter of 70 μm and connected with the light emitting region 11, and two dummy electrodes.

The optical fiber 20 configured to transmit an optical signal includes, for example, a core having a diameter of 62.5 μm, and a clad having a diameter of 80 μm and covering an outer periphery of the core.

The ferrule 30 is a stacked substrate including a silicon substrate 31 which is a semiconductor substrate, and a glass substrate 32 which is a glass substrate. The silicon substrate 31 includes a first principal surface 31SA and a second principal surface 31SB opposite to the first principal surface 31SA. The glass substrate 32 has a third principal surface 32SA and a fourth principal surface 32SB opposite to the third principal surface 32SA, and the third principal surface 32SA is bonded with the second principal surface 31SB of the silicon substrate 31.

In other words, the ferrule 30 has a substantially rectangular parallelepiped shape that includes the first principal surface 31SA and the fourth principal surface 32SB opposite to the first principal surface 31SA. A direction in which the silicon substrate 31 of the ferrule 30 is disposed is referred to as "upper", and a direction in which the glass substrate 32 is disposed is referred to as "lower". Further, one of the four side surfaces of the ferrule 30 is referred to as a side surface 30SS1.

Figure 1:
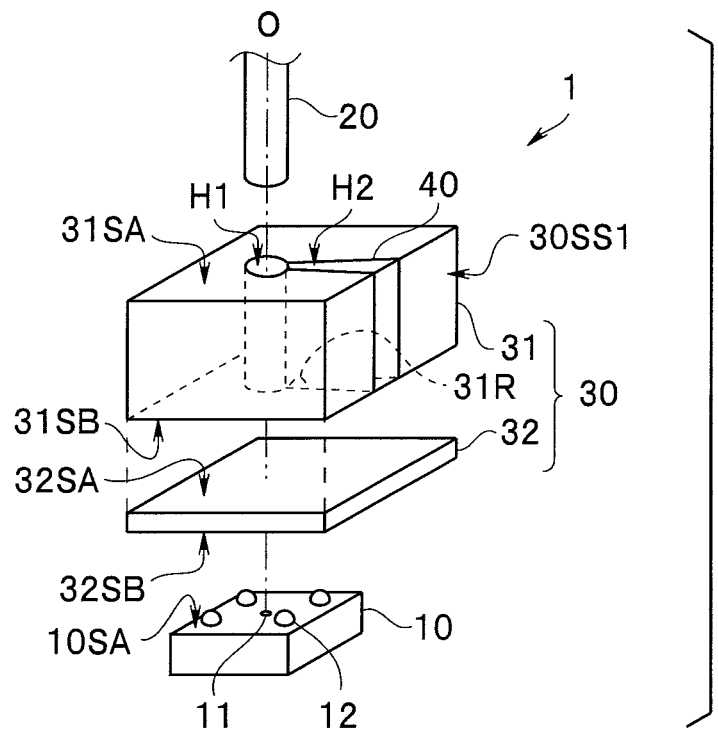
FIG. 1 is a perspective exploded view of an optical transducer according to a first embodiment.
Figure 2:
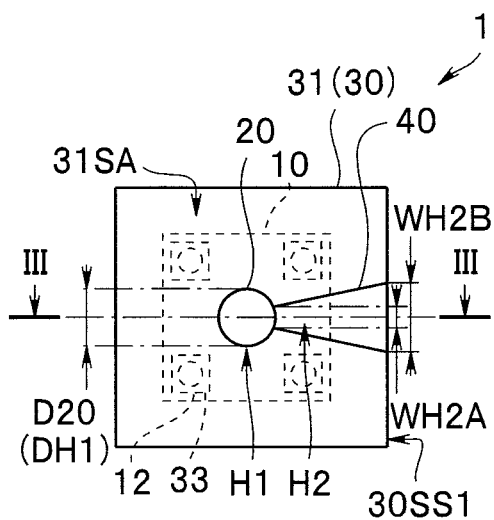
FIG. 2 is a top view of the optical transducer according to the first embodiment.

The ferrule 30 has an ultra-small size with a lateral width of 0.5 mm and a longitudinal width of 0.5 mm in a top view shown in FIG. 2.

The optical element 10 is mounted on the fourth principal surface 32SB of the ferrule 30. In other words, four bonded electrodes 33 are arranged in the fourth principal surface 32SB, and an external electrode 12 of the optical element 10 is bonded to each of the bonded electrodes 33. The bonded electrodes 33 are connected to wiring not shown and configured to transmit drive signals.

The ferrule 30 includes in the first principal surface 31SA an insertion hole H1 that penetrates the silicon substrate 31 from the first principal surface 31SA to the second principal surface 31SB, and the optical fiber 20 is inserted in the insertion hole H1. The insertion hole H1 is bottomed, and a bottom surface of the insertion hole H1 is the third principal surface 32SA of the glass substrate 32. An inner diameter DH1 of the insertion hole H1 is slightly larger than an outer diameter D20 of the optical fiber 20 and is, for example, 85 μm.

Since the insertion hole H1 is located at a position opposed to the light emitting region 11 of the optical element 10, a central axis of the optical fiber 20 inserted into the insertion hole H1 coincides with an optical axis O of the optical element 10, and the optical fiber 20 is optically coupled with the optical element 10.

The silicon substrate 31 has an opening of a trench (slit or pass) H2 penetrating from the first principal surface 31SA to the second principal surface 31SB. The trench H2 is connected with the insertion hole H1. Each of the insertion hole H1 and the trench H2 has an opening in the first principal surface 31SA, and a wall surface is made of silicon. The insertion hole H1 and the trench H2 are bottomed, and the bottom surfaces are the third principal surface 32SA of the glass substrate 32. The trench H2 also has an opening in the side surface 30SS1.

The ferrule 30 does not have the trench H2 in a facing region facing a region where the bonded electrodes 33 are arranged. Therefore, there is no risk that a thin glass substrate 32 is damaged when the optical element 10 is bonded.

As will be described later, the optical fiber 20 is fixed by the transparent resin 40 injected from the trench H2. Therefore, the transparent resin 40 is arranged in the insertion hole H1 and the trench H2. The transparent resin 40 arranged in the insertion hole H1 is not shown because the transparent resin 40 is arranged in a slight gap between an outer surface of the optical fiber 20 and a wall surface of the insertion hole H1.

The position of the distal end surface of the optical fiber 20 may be moved in a period before the transparent resin 40 is cured. Therefore, the transparent resin 40 is preferably of an ultraviolet curable type or of an ultraviolet/thermal dual-curable type.

In an ultra-small size optical transducer, it is not easy to irradiate the transparent resin 40 arranged in the gap between the optical fiber 20 and the insertion hole H1 with ultraviolet rays for curing. If the transparent resin 40 is not sufficiently cured, the optical fiber is not sufficiently fixed, and the reliability of the optical transducer may deteriorate. Further, if air bubbles remain when the uncured transparent resin 40 is injected into the insertion hole H1, the transmission efficiency is decreased.

The ferrule 30 of the optical transducer 1 has not only an opening of the insertion hole H1 but also an opening of the trench H2 in the first principal surface 31SA. Therefore, the ultraviolet rays radiated from above the first principal surface 31SA reach the transparent resin 40 of the insertion hole H1 by passing through the transparent resin 40 arranged in the trench H2. Therefore, the transparent resin 40 in the insertion hole H1 for fixing the optical fiber 20 can be sufficiently cured. Further, since the transparent resin 40 flows into the insertion hole H1 via the trench H2, no air bubble remains in the transparent resin 40.

It works well if a first width WH2A of the trench H2 at a location where the trench H2 is connected to the insertion hole H1, in other words, at a position of the trench H2 farthest from a side surface 30SS1 is smaller than an outer diameter D20 of the optical fiber 20. However, in order to stably hold the optical fiber 20 inserted in the insertion hole H1, the first width WH2A of the trench H2 is preferably 80% or less of the outer diameter D20 of the optical fiber 20 (FIG. 2).

The ferrule 30 of the optical transducer 1 has a convex 31R on the third principal surface 32SA of the glass substrate 32, which is a bottom surface of the trench H2. As will be described later, the convex 31R is made of silicon, since the convex 31R is an etching residue when the trench H2 is formed in the silicon substrate 31 by an etching method.

Thus, the width of the trench H2 is not constant, and the first width WH2A at the location connected to the insertion hole H1 is smaller than a second width WH2B at the side surface 30SS1. The etching rate of a trench with a smaller width is lower than the etching rate of a trench with a larger width (microloading effect). Therefore, as etching of the silicon substrate 31 progresses, what remains at the very end is a convex 31R on the bottom surface of the trench H2 at a location connected to the insertion hole H1.

Further, if the etching is continued, the convex 31R will also be removed by being etched. However, in the optical transducer 1, the etching is ended in a state where the convex 31R has remained.

Figure 6:
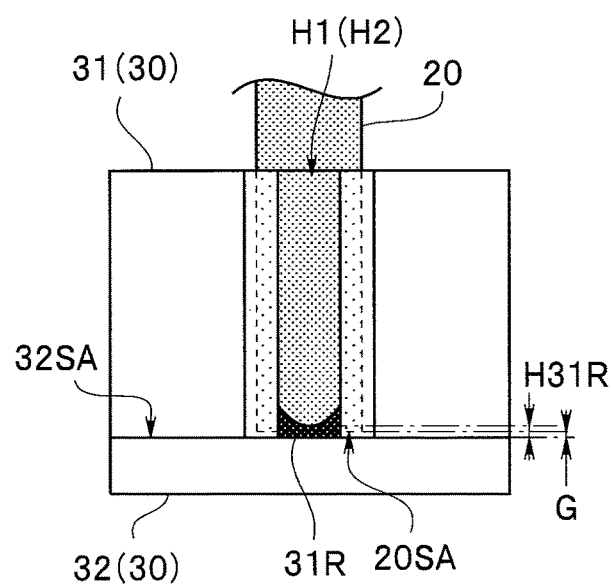
FIG. 6 is a side view of the optical transducer according to the first embodiment.

As shown in FIG. 6, when a distal end surface 20SA of the optical fiber 20 is observed from the opening of the trench H2 in the side surface 30SS1, at least a part of the distal end surface 20SA is shielded by the convex 31R.

Therefore, it has been confirmed that a gap G from the distal end surface 20SA to the third principal surface 32SA is not more than a height H31R of the convex 31R. Therefore, the optical transducer 1 exhibits excellent transmission efficiency.

Figure 3:
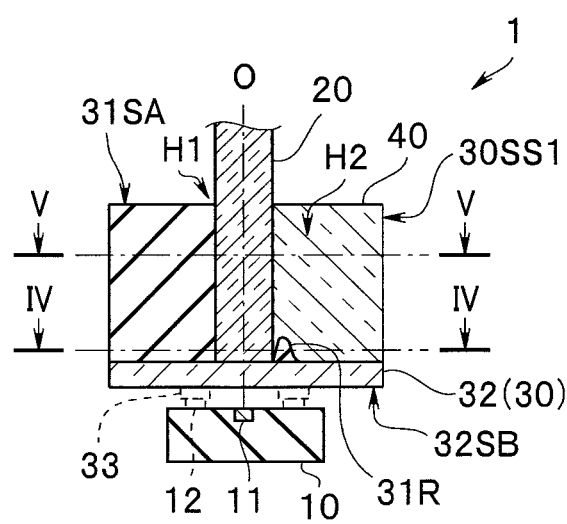
FIG. 3 is a sectional view along a III-III line of FIG. 2 of the optical transducer according to the first embodiment.
Figure 4:
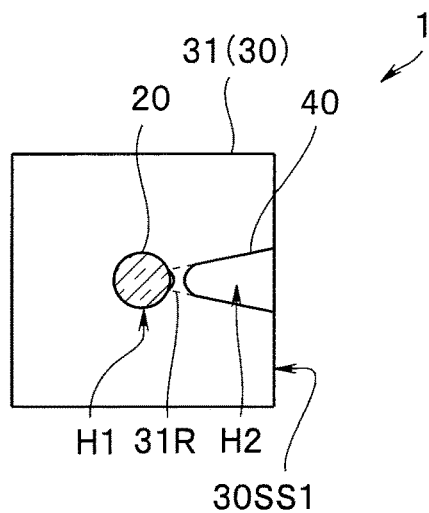
FIG. 4 is a sectional view along a IV-IV line of FIG. 3 of the optical transducer according to the first embodiment.
Figure 5:
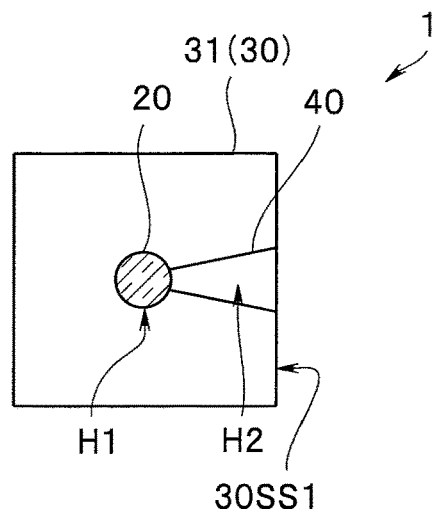
FIG. 5 is a sectional view along a V-V line of FIG. 3 of the optical transducer according to the first embodiment.

The height H31R of the convex 31R is preferably more than 1 μm and less than 15 μm. When the height H31R of the convex 31R is not more than 1 μm, it is not easy to confirm the convex 31R from the side surface 30SS1, and when not less than 15 μm, the gap G is large and the transmission efficiency of the optical transducer 1 is poor. As shown in FIGS. 3 and 6, the height H31R varies in a width direction and a length direction of the trench H2, and the above described height H31R is the minimum height when observed from the side surface 30SS1.

<Manufacturing Method of Optical Transducer for Endoscope>

Figure 7:
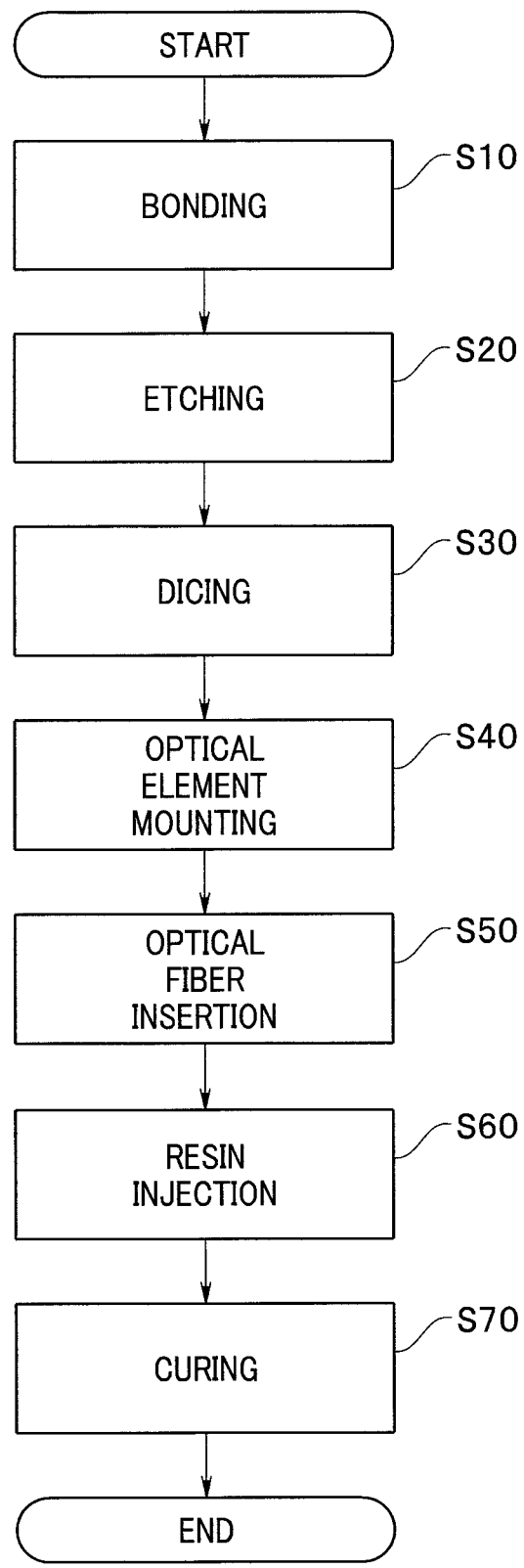
FIG. 7 is a manufacturing flowchart of the optical transducer according to the first embodiment.

A manufacturing method of an optical transducer 1 will be described with reference to a flowchart of FIG. 7.

<Step S10> Bonding Step

The ferrule 30 of the optical transducer 1 is produced by a wafer process. First, a bonded wafer is produced by, for example, anodically bonding a silicon wafer with a glass wafer.

As the thickness of the glass substrate 32 increases, the transmission efficiency decreases. Therefore, the glass wafer of the bonded wafer is thinned to a thickness of more than 5 μm and less than 50 μm. If the thickness of the glass substrate 32 is less than 50 m, the glass substrate 32 can transmit not less than 95% of light of a wavelength of optical signal, and at the same time, achieve excellent transmission efficiency since the distance between the light emitting surface 10SA and the distal end surface 20SA of the optical fiber 20 can be decreased. Note that if the thickness of the glass wafer is more than 5 μm, the glass wafer is unlikely to be damaged in a subsequent step. It goes without saying that the glass wafer may have a thickness not less than the above described thickness in a state of a bonded wafer when the thinning is performed after the etching step S20.

The thickness of the silicon wafer is preferably more than 100 μm in order that the silicon substrate 31 stably holds the optical fiber 20.

Note that the wafer to be the semiconductor substrate is not limited to a silicon wafer, and may be a wafer made of an etchable semiconductor. Further, as will be described later, as a bonded wafer, an SOI wafer which is a stacked substrate of a first silicon layer/a silicon oxide layer/a second silicon layer can also be used.

<Step S20> Etching Step

The insertion hole H1 and the trench H2 are formed by using an etching method. An etching mask made of a photoresist or a silicon oxide layer is arranged on the surface of a silicon wafer. Then, for example, by using a reactive ion etching (RIE) method, it is possible to easily and accurately form an insertion hole H1 and a trench H2, wall surfaces of which are substantially perpendicular to the principal surface. Since the glass wafer serves as an etching stop layer, an insertion hole H1 and a trench H2, bottom surfaces of which are a third principal surface 32SA, are formed.

In the etching step S20 of the optical transducer 1, the etching process is ended in a state in which the third principal surface 32SA is exposed on the bottom surface of the trench H2, and the convex 31R remains on a part of the bottom surface. As described above, due to the microloading effect, if the depth of the trench is the same, the etching rate becomes low when the size of the opening of the etching mask is small, that is, when the width of the trench is narrow. For this reason, in a final stage of etching, the convex 31R remains at a location where the width of the opening of the trench H2 is small and the trench H2 is connected to the insertion hole H1.

The insertion hole H1 or the like may be formed by using a wet etching method. The shape of an inner surface of the insertion hole H1 may be a cylinder as well as a prism as long as the optical fiber 20 can be held by the inner surface of the insertion hole H1.

<Step S30> Dicing Process

A plurality of ferrules 30 are produced by cutting a bonded wafer in which a plurality of insertion holes H1 and a plurality of trenches H2 are formed. Note that from the viewpoint of productivity, it is preferable that the ferrule 30 should be produced by cutting a bonded wafer in which a silicon wafer and a glass wafer are bonded. However, the ferrule 30 may be produced by processing a bonded substrate in which a silicon substrate 31 produced by cutting a silicon wafer and a glass substrate 32 produced by cutting a glass wafer are bonded. In other words, the dicing process S30 of bonded wafer is not an indispensable step. The external shape of the ferrule 30 is a rectangular parallelepiped shape, but may be a cylinder shape or a polygonal prism shape.

<Step S40> Optical Element Mounting Process

An optical element 10 is mounted on a fourth principal surface 32SB of the ferrule 30.

A plurality of bonded electrodes 33 are arranged in advance at predetermined positions on the fourth principal surface 32SB. When an external electrode 12 of the optical element 10 is, for example, ultrasonically bonded to one of the bonded electrodes 33, the light emitting region 11 of the optical element 10 is fixed at a position facing the insertion hole H1.

At the time of bonding of the optical element 10, stress is applied to the glass substrate 32 of the ferrule 30. However, as shown in FIG. 2, the ferrule 30 has no insertion holes H1 and trench H2 in a facing region facing a region of the fourth principal surface 32SB where the bonded electrode 33 is arranged, that is, a region to which the external electrode 12 of the optical element 10 is bonded. A region of the glass substrate 32 where the bonded electrode 33 is arranged is reinforced due to the presence of the silicon substrate 31. Therefore, there is no risk that the thin glass substrate 32 is damaged at the time of bonding of the optical element 10. The optical transducer 1 is highly reliable because high bonding pressure can be set when the optical element 10 is, for example, ultrasonically bonded.

<Step S50> Optical Fiber Insertion Step

The optical fiber 20 is inserted into the insertion hole H1. By observing the distal end surface 20SA of the optical fiber 20 from the side surface 30SS1 of the ferrule 30, it is confirmed that at least a part of the distal end surface 20SA is shielded by a convex 31R. The observation may be performed by viewing directly through a microscope, or by using an image displayed on a monitor screen. Further, such shielding does not need to be confirmed by an operator, and may be automatically confirmed by image analysis.

The smaller the gap G from the distal end surface 20SA to the third principal surface 32SA, the better the transmission efficiency. However, there is a risk that the glass substrate 32 is damaged if the optical fiber 20 is strongly pushed into the insertion hole H1 to ensure that the distal end surface 20SA is in contact with the third principal surface 32SA. In the present embodiment, the optical fiber 20 can be securely inserted without damaging the glass substrate 32 by completing the insertion when it is confirmed that at least a part of the distal end surface 20SA of the optical fiber 20 is shielded by the convex 31R.

The insertion operation of the optical fiber 20 is ended when it is confirmed that at least a part of the distal end surface 20SA is shielded by the convex 31R, and the optical fiber 20 is held at the insertion position. In other words, until the curing treatment S70 is completed, the position of the optical fiber 20 relative to the ferrule 30 is fixed by using, for example, a holding jig (not shown).

<Step S60> Resin Injection Process

A liquid transparent resin 40 before curing is injected from a trench H2 of a ferrule 30, and the transparent resin 40 is arranged in the insertion hole H1.

As the transparent resin 40, various ultraviolet curable resins each having a high light transmittance and a predetermined refractive index, or ultraviolet/thermal dual-curable type resins, for example, silicone resin or epoxy resin are used.

Since the transparent resin 40 flows into the insertion hole H1 via the trench H2, no air bubble remains. Further, since the insertion hole H1 and the trench H2 each have an opening in the first principal surface 31SA, the excessively injected transparent resin 40 overflows onto the first principal surface 31SA. Therefore, there is no risk that the thin glass substrate 32 is damaged by the injection pressure when the transparent resin 40 is injected.

Note that the optical fiber insertion step S50 may be performed after the resin injection step S60. When the optical fiber 20 is inserted into the insertion hole H1 into which the transparent resin 40 has been injected, there is a risk that the glass substrate 32 is damaged since pressure is applied by the transparent resin 40 pressed by the optical fiber 20.

In the manufacturing method of the present embodiment, the extruded transparent resin 40 overflows from the opening of the trench H2 in the first principal surface 31SA and the opening of the trench H2 in the side surface 30SS1. Therefore, when the optical fiber 20 is inserted into the insertion hole H1, there is no risk that the thin glass substrate 32 is damaged by the insertion pressure.

Until the curing treatment is completed, the opening of the trench H2 in the side surface 30SS1 is closed by using a transparent jig (not shown).

According to the manufacturing method of the present embodiment, the optical transducer 1 in which a gap G is not more than the height H31R of the convex 31R can be manufactured at a high yield.

<Step S70> Curing Step

The transparent resin 40 is cured in a state in which the distal end surface 20SA is shielded by the convex 31R. In other words, the transparent resin 40 is irradiated with ultraviolet rays. The gap between the insertion hole H1 and the optical fiber 20 is extremely small. Therefore, it is not easy to irradiate the transparent resin 40 in the gap with ultraviolet rays.

However, the ferrule 30 has a trench H2 connected to the insertion hole H1. Therefore, the transparent resin 40 of the insertion hole H1 can be efficiently irradiated with ultraviolet rays from the openings of the trench H2 in the first principal surface 31SA and the side surface through the trench H2.

In other words, the trench H2 is effective not only in arranging the transparent resin 40 in the insertion hole H1, but also in irradiating the transparent resin 40 of the insertion hole H1 with ultraviolet rays.

Note that in a case in which the transparent resin 40 is an ultraviolet/thermal dual-curable type resin, for example, a thermal curing step at 100° C. for 1 hour is further performed after the ultraviolet rays irradiation step.

The optical transducer 1 is able to securely perform the insertion step S60 without damaging the glass substrate 32, and therefore is easy to manufacture.

Modifications of First Embodiment

Since optical transducers 1A to 1E according to modifications of the first embodiment are similar to the optical transducer 1 and have the same effect, the components having the same function are designated by the same reference symbol, and description of those components will be omitted.

Modification 1 of First Embodiment

Figure 8:
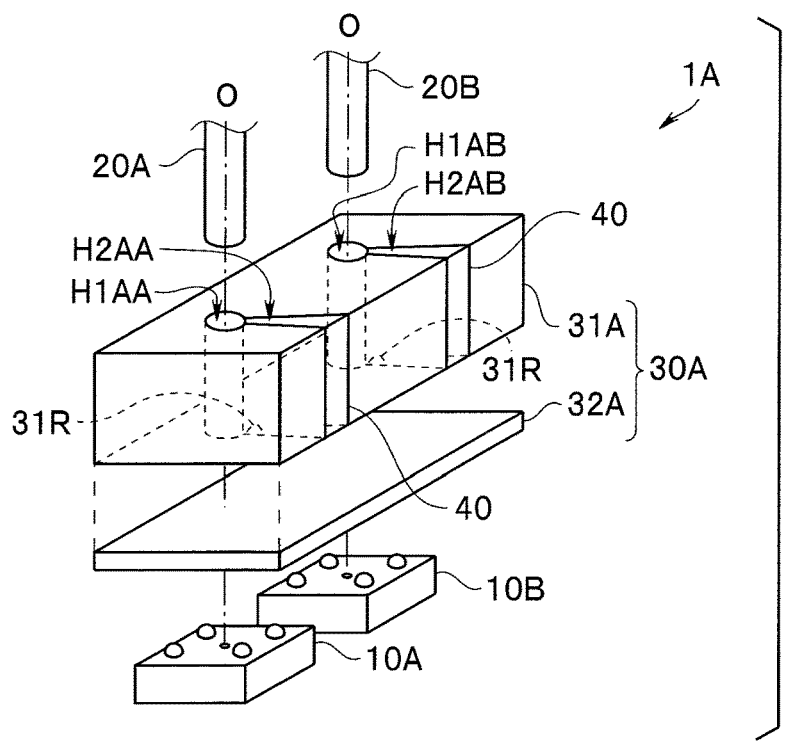
FIG. 8 is a perspective exploded view of an optical transducer according to Modification 1 of the first embodiment.

An optical transducer 1A according to Modification 1 of the first embodiment shown in FIG. 8 includes two optical elements 10A and 10B, two optical fibers 20A and 20B, and a ferrule 30A (31A. 32A). The ferrule 30A, which includes a silicon substrate 31A and a glass substrate 32A, has two insertion holes H1AA and H1AB and two trenches H2AA and H2AB.

The optical fiber 20A inserted into the insertion hole H1AA transmits a first optical signal outputted by the optical element 10A. The optical fiber 20B inserted into the insertion hole H1AB transmits a second optical signal outputted by the optical element 10B.

Needless to say, the optical transducer 1A has the effect of the optical transducer 1, and the optical transducer 1A can transmit more signals than the optical transducer 1.

An optical transducer according to embodiments of the present invention may include three or more optical elements and three or more optical fibers. An optical transducer according to the embodiments includes at least one optical element, at least one optical fiber, and a ferrule.

Modification 2 of First Embodiment

Figure 9:
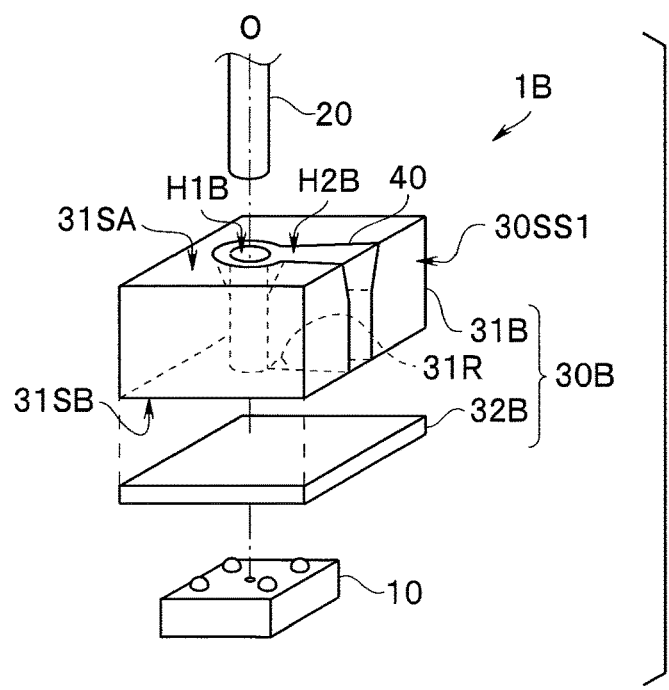
FIG. 9 is a perspective exploded view of an optical transducer according to Modification 2 of the first embodiment.

A ferrule 30B of an optical transducer 1B according to Modification 2 of the first embodiment shown in FIG. 9 includes a silicon substrate 31B and a glass substrate 32B. The insertion hole H1B and the trench H2B of the silicon substrate 31B each have a tapered shape in which an opening in the first principal surface 31SA is larger than an opening in the second principal surface 31SB.

For example, a silicon wafer in which a principal surface is a (100) plane is subjected to anisotropic wet-etching using an alkaline aqueous solution such as a KOH or TMAH (tetramethylammonium hydroxide) solution. In anisotropic wet etching, the etching rate of the (100) plane is faster than the etching rate of a (111) plane. For this reason, a concave portion having a V-shaped cross section is formed. An angle θ between wall surfaces of the concave portion is 54.7 degrees. Subsequently, an anisotropic dry etching process is performed using a same etching mask 39 as it is. For example, by using a deep reactive ion etching (D-RIE) method, a hole and a trench in each of which wall surfaces are perpendicular to the principal surface are formed.

Although the above described method is an example of combining anisotropic wet etching and anisotropic dry etching, a method of forming a taper by performing anisotropic dry etching and isotropic dry etching may also be used. Since a hole formed by anisotropic dry etching has a high aspect ratio (depth/opening size), it is difficult for the etching gas to reach the bottom of the hole in isotropic dry etching. Therefore, only an upper portion of the hole is isotropically etched. In any of the above described methods, a taper can be formed in the insertion hole H1B and the trench H2B, respectively.

Since the optical transducer 1B has a tapered opening of the insertion hole H1B, inserting the optical fiber 20 is easy. Further, since the optical transducer 1B also has a tapered opening of the trench H2B, injecting the transparent resin 40 by means of a dispenser or the like is easy.

Modification 3 of First Embodiment

Figure 10:
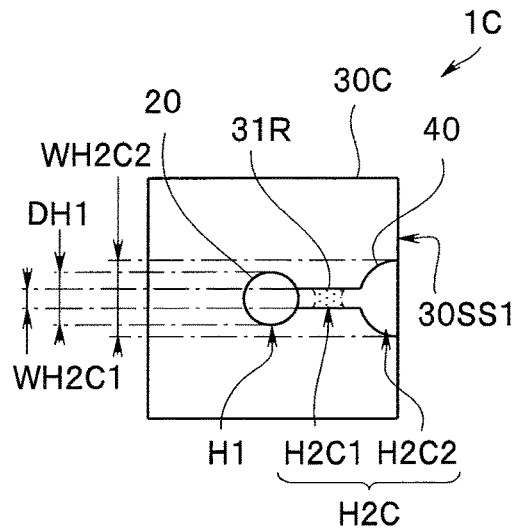
FIG. 10 is a top view of an optical transducer according to Modification 3 of the first embodiment.

In an optical transducer 1C according to Modification 3 of the first embodiment shown in FIG. 10, a trench H2C includes a first trench H2C1 connected to an insertion hole H1 and a second trench H2C2 connected to the first trench H2C1 and having an opening in a side surface 30SS1.

The width of the first trench H2C1 is constant, but a first width WH2C1 of a location of the first trench H2C1 connected to the insertion hole H1 is smaller than an outer diameter D20 of the optical fiber 20. The second trench H2C2 has a semicircular column shape in which a width WH2C2 in the side surface 30SS1 is larger than the first width WH2C1.

In a ferrule 30C, a convex 31R remains on a bottom surface of the first trench H2C1.

Since the optical transducer 1C has a large width WH2C2 of the second trench H2C2 in the side surface 30SS1, observing the distal end surface of the optical fiber 20 is easy and injecting the transparent resin 40 is also easy.

Modification 4 of First Embodiment

Figure 11:
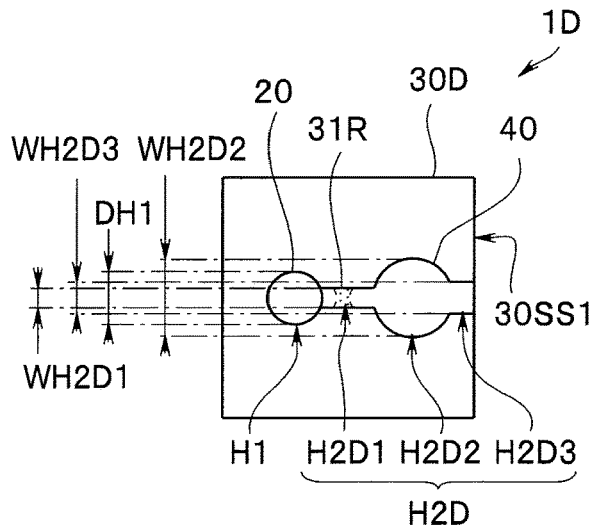
FIG. 11 is a top view of an optical transducer according to Modification 4 of the first embodiment.

In an optical transducer 1D according to Modification 4 of the first embodiment shown in FIG. 11, a trench H2D has a first trench H2D1 connected to an insertion hole H1, a second trench H2D2 connected to the first trench H2D1, and a third trench H2D3 connected to the second trench H2D2 and having an opening in a side surface 30SS1.

A width of the first trench H2D1 is constant, but a first width WH12D1 of a location of the first trench H2D1 connected to the insertion hole H1 is smaller than an outer diameter D20 of the optical fiber 20. The second trench H2D2 has a substantially columnar shape in which a width WH2D2 is larger than the outer diameter D20 of the optical fiber 20. A width WH2D3 of the third trench H2D3 is constant, but is larger than the first width WH2D1 and smaller than the width WH2D2 of the second trench H2D2.

In a ferrule 30D, a convex 31R remains on the bottom surface of the first trench H2D1.

Since the optical transducer 1D can insert a micro syringe into the second trench H2D2, injecting the transparent resin 40 is easy.

Modification 5 of First Embodiment

Figure 12:
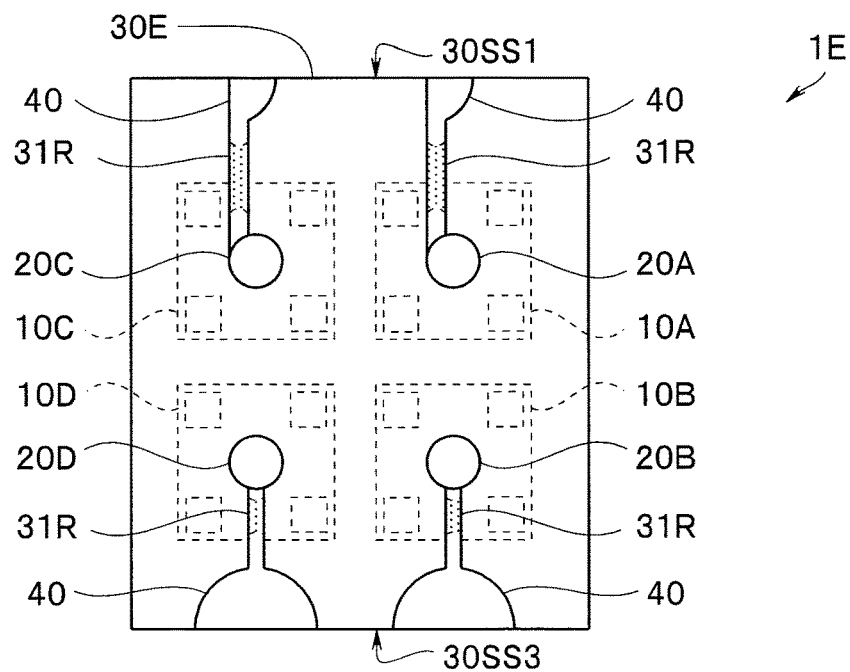
FIG. 12 is a top view of an optical transducer according to Modification 5 of the first embodiment.

An optical transducer 1E according to Modification 5 of the first embodiment shown in FIG. 12 includes four optical elements 10A to 10D, four optical fibers 20A to 20D, and a ferrule 30E.

A ferrule 30E has four insertion holes and four trenches. Openings of the four trenches are in either of the two side surfaces 30SS1 and 30SS2. Moreover, the four trenches do not have a same shape.

However, since each trench has a convex 31R, the four optical fibers 20A to 20D can be easily and safely inserted into the respective insertion holes up to a predetermined position.

Modification 6 of the First Embodiment

Figure 13:
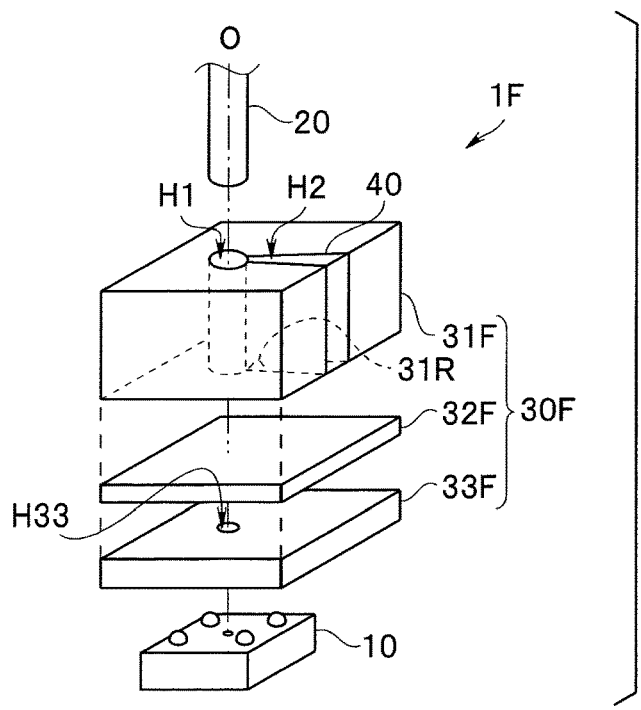
FIG. 13 is a top view of an optical transducer according to Modification 6 of the first embodiment.

A ferrule 30F of an optical transducer 1F according to Modification 6 of the first embodiment shown in FIG. 13 is produced by processing an SOI wafer.

The ferrule 30F includes an SOI which is a stacked substrate in which a first silicon layer (semiconductor substrate: silicon substrate) 31F, a silicon oxide layer (glass substrate) 32F, and a second silicon layer 33F are stacked. The second silicon layer 33F has a through hole H33 that serves as an optical path.

In a method for producing the ferrule 30F, in an etching step S20, an insertion hole H1 and a trench H2 each penetrating a first silicon layer 31F are formed, with a silicon oxide layer (glass substrate: glass substrate) as an etching stop layer, in a first silicon layer (semiconductor substrate: silicon substrate) of the SOI wafer including the first silicon layer/silicon oxide layer/second silicon layer. The bottom surfaces of the insertion hole H1 and the trench H2 will be the silicon oxide layer (the third principal surface of the glass substrate).

In the etching step S20, the etching process is ended in a state in which a silicon oxide layer 32F is exposed on the bottom surface of the trench H2, and the convex 31R remains on a part of the bottom surface.

Further, a through hole H33 is formed in the second silicon layer 33F. Note that the second silicon layer 33F may be removed. Further, when the optical signal is infrared light, since silicon is a material that is substantially transparent to infrared light, the transmission efficiency will not decrease even if the second silicon layer 33F is present in the optical path.

The optical transducer 1F is easy to manufacture because the ferrule 30F is produced using an SOI substrate.

Second Embodiment

Since an optical transducer 1G according to a modification of a second embodiment is similar to the optical transducer 1 and has a same effect, the components having the same function are designated by the same reference symbol and description of those components will be omitted.

Figure 14:
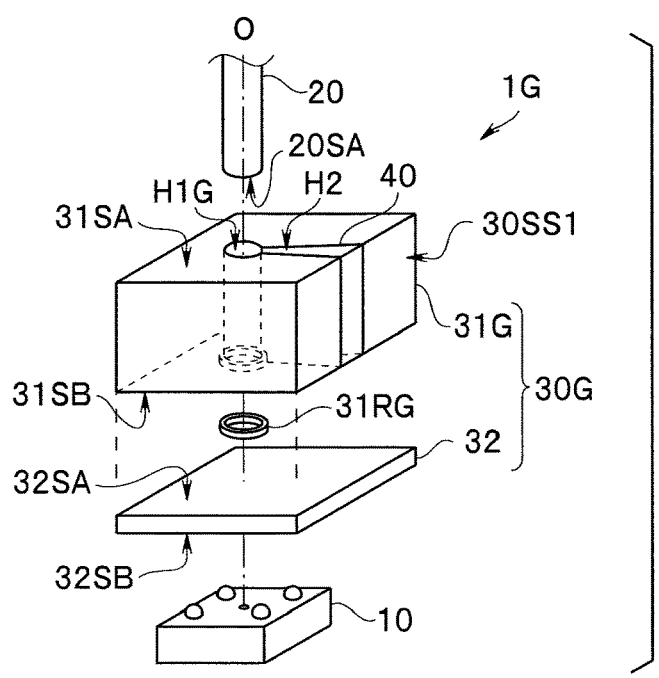
FIG. 14 is a perspective exploded view of an optical transducer according to a second embodiment.

A ferrule 30G of the optical transducer 1G shown in FIG. 14 includes a silicon substrate 31G and a glass substrate 32. However, a convex 31RG that shields the distal end surface 20SA of the optical fiber 20 when observed from the side surface 30SS1 is made of colored glass instead of silicon.

The convex 31RG has a substantially annular shape extending on the bottom surface of an insertion hole H1G, and a distal end portion of the optical fiber 20 is inserted into an inner peripheral portion of the convex 31RG. In other words, the inner diameter of the convex 31RG is slightly larger than the outer diameter of the optical fiber 20. Further, the inner diameter of the insertion hole H1G is larger than the inner diameter of the convex 31RG.

Thus, the convex 31RG has not only a function of shielding the distal end surface 20SA of the optical fiber 20 but also a function of holding the optical fiber 20 at a predetermined position.

The convex 31RG is produced by forming an annular concave portion on a second principal surface 31SB of the silicon substrate 31G and filling the concave portion with colored glass before bonding the silicon substrate 31G with the glass substrate 32.

The convex 31RG is not limited to colored glass as long as it is a light-shielding material other than silicon, and may be, for example, a light-shielding resin.

Third Embodiment

Next, an endoscope 9 of a third embodiment will be described. As shown in FIG. 15, the endoscope 9 has an optical transducer 1 (1A to 1G) at a distal end portion 9A of an insertion portion 9B.

The endoscope 9 includes the insertion portion 9B in which an image pickup device 2 having a high number of pixels is arranged at the distal end portion 9A, an operation portion 9C arranged on a proximal end side of the insertion portion 9B, and a universal cord 9D extending from the operation portion 9C.

An electric signal outputted by the image pickup device 2 is converted into an optical signal by an E/O type optical transducer 1 (1A to 1G). Then, the optical signal is passed through an optical fiber 20 and is converted into an electric signal again by an O/E type optical transducer 1X arranged in the operation portion 9C and having a PD as an optical element, thereafter being transmitted through a metal wiring. In other words, in a small-diameter insertion portion 9B, the signal is transmitted through the optical fiber 20.

Further, an electric signal outputted by the image pickup device 2 is converted into an optical signal by an E/O type optical transducer 1 (1A to 1G). Then, the optical signal is passed through the insertion portion 9B, the operation portion 9C, and the universal cord 9D via the optical fiber 20, and thereafter may be converted into an electric signal by an O/E type optical transducer 1X arranged in a processor (not shown) and having a PD as the optical element. The processor performs signal processing for displaying the electric signal converted by the O/E type optical transducer 1X on a display device, for example, a monitor.

As already explained, the optical transducer 1 (1A to 1G) is small sized and exhibits high reliability and high productivity. Thus, the endoscope 9 is minimally invasive because the insertion portion has a small diameter, and exhibits high reliability and high productivity.

Note that while the optical transducer 1X is arranged in the operation portion 9C having a relatively large disposition space, the optical transducer 1X may have a same configuration as the configuration of the optical transducer 1 or the like of the present invention. Further, although the endoscope 9 is a flexible endoscope, the endoscope 9 may be a rigid endoscope, and may be used either for medical purposes or for industrial purposes. Further, a control signal to the image pickup device 2 may be converted into an optical signal by the optical transducers 1 (1A to 1G) arranged in the operation portion 9C, and the optical signal may be converted into an electric signal by the optical transducer 1X arranged in the distal end portion 9A.

The optical transducer 1 or the like is a light emitting element having a light emitting region 11 in which the optical element 10 or the like outputs an optical signal. In contrast to this, even if the optical element of the optical transducer is a light receiving element such as a photodiode, having a light receiving portion to which an optical signal is inputted, the light receiving element exhibits the same effect as the effect of the optical transducer 1 or the like.

In other words, the optical element may include a light emitting region configured to output an optical signal or a light receiving unit into which an optical signal is inputted, and an external electrode connected to the light emitting region or the light receiving unit.

The present invention is not limited to the above-described embodiments, and various modifications, combinations, and applications can be made without departing from the spirit of the invention.

What is claimed is:

1. An optical transducer for use with an endoscope, the optical transducer comprising:
   an optical element;
   an optical fiber optically coupled with the optical element; and
   a ferrule comprising:
      a semiconductor substrate including a first principal surface and a second principal surface opposite to the first principal surface, the semiconductor substrate having an insertion hole penetrating the semiconductor substrate from the first principal surface to the second principal surface, the optical fiber is disposed in the insertion hole, and
      a glass substrate including a third principal surface and a fourth principal surface opposite to the third principal surface, and the third principal surface is bonded with the second principal surface, the optical element is mounted on the fourth principal surface,
   wherein the semiconductor substrate includes a trench having an opening in a side surface of the semiconductor substrate, the trench extending from the opening to the insertion hole, and
   at least a portion of a circumferential surface of the optical fiber is exposed through the opening.

2. The optical transducer according to claim 1, wherein the semiconductor substrate comprises a projection extending within the trench from the second principal surface towards the first principal surface.

3. The optical transducer according to claim 2, wherein the semiconductor substrate and the projection are made of silicon.

4. The optical transducer according to claim 2, wherein the semiconductor substrate is made of silicon, and the projection is made of a material different from the semiconductor substrate.

5. The optical transducer according to claim 4, wherein further comprising a substantially annular member surrounding the insertion hole and extending from the second principal surface towards the first principal surface,
   wherein a portion of the annular member corresponding to the trench comprises the projection; and
   a distal end portion of the optical fiber is inserted into an inner peripheral portion of the annular member.

6. The optical transducer according to claim 5, wherein an inner diameter of the insertion hole is larger than an inner diameter of the annular member.

7. The optical transducer according to claim 2, wherein a height of the projection is more than 1 µm and less than 15 µm.

8. The optical transducer according to claim 1, wherein a first width of the trench at a location connected with the insertion hole is smaller than an outer diameter of the optical fiber.

9. The optical transducer according to claim 8, wherein the first width is smaller than a second width of the trench at the side surface.

10. The optical transducer according to claim 1, wherein the trench includes a first trench connected with the insertion hole and a second trench connected with the first trench and having the opening in the side surface,
    a first width of the first trench at a location connected with insertion hole is smaller than an inner diameter of the insertion hole, and
    a second width of the second trench at the side surface is larger than an inner diameter of the insertion hole.

11. The optical transducer according to claim 1, wherein the trench includes a first trench connected with the insertion hole, a second trench connected with the first trench, and a third trench connected with the second trench and having the opening in the side surface,
    a first width of the first trench at a location connected with the insertion hole is smaller than an inner diameter of the insertion hole,
    a second width of the second trench is larger than an inner diameter of the insertion hole, and
    a third width of the third trench is larger than the first width and smaller than the second width.

12. The optical transducer according to claim 1, wherein the insertion hole has a first insertion hole opening at the first principal surface larger than a second insertion hole opening at the second principal surface.

13. The optical transducer according to claim 1, wherein:
    the optical element comprises a plurality of optical elements;
    the optical fiber comprises a plurality of optical fibers respectively corresponding to the plurality of optical elements; and
    the ferrule comprising an insertion hole corresponding to each of the plurality of optical fibers and a trench corresponding to each of the plurality of insertion holes.

14. The optical transducer according to claim 1, wherein the optical fiber is fixed to the ferrule with a transparent resin arranged in the insertion hole and in the trench.

15. The optical transducer according to claim 1, wherein the third principal surface is a bottom surface of the trench.

16. The optical transducer according to claim 15, wherein the trench comprises tapered surfaces relative to a direction from the side surface to the insertion hole.

17. The optical transducer according to claim 1, wherein the semiconductor substrate comprises a projection extending within the trench from the second principal surface towards the first principal surface,
    the projection has a height projecting from the third principal surface such that a distal end face of the optical fiber is shielded by the projection when viewed in a direction from the side surface.

18. An endoscope comprising:
    an optical transducer, wherein the optical transducer comprises:
       an optical element;
       an optical fiber optically coupled with the optical element; and
       a ferrule comprising:
          a semiconductor substrate including a first principal surface and a second principal surface opposite to the first principal surface, the semiconductor substrate having an insertion hole penetrating the semiconductor substrate from the first principal surface to the second principal surface, the optical fiber is disposed in the insertion hole, and a glass substrate including a third principal surface and a fourth principal surface opposite to the third principal surface, and the third principal surface is bonded with the second principal surface, the optical element is mounted on the fourth principal surface, wherein the semiconductor substrate includes a trench having an opening in a side surface of the semiconductor substrate, the trench extending from the opening to the insertion hole, and at least a portion of a circumferential surface of the optical fiber is exposed through the opening.

19. The endoscope according to claim 18, wherein the trench comprises tapered surfaces relative to a direction from the side surface to the insertion hole.

20. A manufacturing method of an optical transducer for use with an endoscope, wherein the optical transducer comprises:

an optical element;

an optical fiber optically coupled with the optical element; and a ferrule comprising:

a semiconductor substrate including a first principal surface and a second principal surface opposite to the first principal surface, the semiconductor substrate having an insertion hole penetrating the semiconductor substrate from the first principal surface to the second principal surface, the optical fiber is disposed in the insertion hole, and a glass substrate including a third principal surface and a fourth principal surface opposite to the third principal surface, and the third principal surface is bonded with the second principal surface, the optical element is mounted on the fourth principal surface, the manufacturing method comprising:

forming a trench by etching on a stacked substrate in which the semiconductor substrate and the glass substrate are stacked, the trench being etched to have an opening in a side surface of the semiconductor substrate and the trench extending from the opening to the insertion hole, mounting the optical element on the stacked substrate;

inserting the optical fiber into the insertion hold while observing a distal end surface of the optical fiber from the opening in the trench;

arranging uncured transparent resin in the insertion hole via the trench; and curing the transparent resin of an ultraviolet curable type or an ultraviolet/thermal dual-curable type.

* * * * *